(12) United States Patent
Crafton (10) Patent No.: US 10,314,729 B2
(45) Date of Patent: Jun. 11, 2019

(54) KNEE BRACE DEVICES AND SYSTEMS AND METHODS OF USING THE SAME

(71) Applicant: Jerry L. Crafton, Terre Haute, IN (US)

(72) Inventor: Jerry L. Crafton, Terre Haute, IN (US)

(*) Notice: Subject to any disclaimer, the term of this patent is extended or adjusted under 35 U.S.C. 154(b) by 680 days.

(21) Appl. No.: 14/215,003

(22) Filed: Mar. 16, 2014

(65) Prior Publication Data

US 2014/0276313 A1  Sep. 18, 2014

Related U.S. Application Data (60) Provisional application No. 61/788,243, filed on Mar. 15, 2013.

(51) Int. Cl.
*A61F 5/01* (2006.01)
*A61F 5/37* (2006.01)

(52) U.S. Cl.
CPC .......... *A61F 5/0106* (2013.01); *A61F 5/0123* (2013.01); *A61F 5/3715* (2013.01)

(58) Field of Classification Search
CPC .... A61F 5/0102; A61F 5/0125; A61F 5/0127; A61F 5/013; A61F 5/0193; A61F 7/02; A61F 2005/0179; A61F 2/60; A61F 2/78; A61F 2/80; A61F 5/0111; A61F 5/012; A61F 5/0123; A61F 5/3723; A61F 2/7843; A61F 2002/745; A61F 2002/747; A61F 2005/0134; A61F 2005/016; A61F 2005/0167; A61F 2/68
USPC ............ 602/4–5, 16, 20–28, 60–62; 128/882
See application file for complete search history.

(56) References Cited

U.S. PATENT DOCUMENTS

| | | | |
|---|---|---|---|
| 1,660,721 A | | 2/1928 | Schrag |
| 2,008,897 A | * | 7/1935 | Carnes ...................... A61F 2/64 |
| | | | 623/30 |
| 2,543,847 A | | 3/1951 | Hallstedt |
| 3,275,205 A | * | 9/1966 | Howd ..................... A62B 35/00 |
| | | | 224/250 |
| 3,739,772 A | * | 6/1973 | Ennis .................... A61F 13/041 |
| | | | 602/4 |
| 4,483,336 A | * | 11/1984 | Deitch ...................... A61F 2/78 |
| | | | 2/310 |
| 5,230,700 A | | 7/1993 | Humbert et al. |
| D377,833 S | | 2/1997 | Schwartz |

(Continued)

FOREIGN PATENT DOCUMENTS

| | | |
|---|---|---|
| BE | 901.878 | 1/1985 |
| DE | 3904491 C2 | 1/1991 |

(Continued)

*Primary Examiner* — Ophelia A Hawthorne
*Assistant Examiner* — Caitlin A Carreiro
(74) *Attorney, Agent, or Firm* — Reichel Stohry LLP; Mark C. Reichel; Natalie J. Dean (57) ABSTRACT

Knee brace devices and systems and methods of using the same. In an exemplary embodiment of a knee brace system of the present disclosure, the system comprises a knee brace configured to fit around at least part of a user's knee, and a strap having an optional strap connection portion coupled thereto, the strap configured to couple to the knee brace or a component coupled thereto and further configured to wrap around the user's shoulder so that the knee brace is maintained around at least part of the user's knee.

19 Claims, 6 Drawing Sheets

(56) References Cited

U.S. PATENT DOCUMENTS

| | | | |
|---|---|---|---|
| 5,882,321 A | 3/1999 | Fisk | |
| 6,146,346 A | 11/2000 | Godwin | |
| 6,213,922 B1 | 4/2001 | Afanassenko et al. | |
| 6,428,495 B1 * | 8/2002 | Lynott | A61F 5/3715 128/875 |
| 6,837,862 B2 * | 1/2005 | Driver, Jr. | A61F 5/3715 128/875 |
| 2002/0183670 A1 * | 12/2002 | Driver, Jr. | A61F 5/3715 602/4 |
| 2011/0282256 A1 | 11/2011 | Carroll | |

FOREIGN PATENT DOCUMENTS

| | | |
|---|---|---|
| DE | 29824758 U1 | 8/2002 |
| FR | 488.296 | 9/1918 |

* cited by examiner

KNEE BRACE DEVICES AND SYSTEMS AND METHODS OF USING THE SAME

PRIORITY

The present application is related to, and claims the priority benefit of, U.S. Provisional Patent Application Ser. No. 61/788,243, filed Mar. 15, 2013, the contents of which are hereby incorporated by reference in their entirety into this disclosure.

BACKGROUND

Knee braces, when worn to provide a wearer/user with increased mobility and/or comfort, do not always work as intended, as depending on the size of the brace or the proportions of the wearer, said braces can slip or otherwise not remain in place as desired. As such, a novel knee brace system useful to maintain a proper position of a knee brace, including a knee brace worn by an obese or otherwise overweight patient, all while not negatively impacting mobility, would be commercially appreciated.

BRIEF SUMMARY

In an exemplary embodiment of a knee brace system of the present disclosure, the system comprises a knee brace configured to fit around at least part of a user's knee, and a strap having an optional strap connection portion coupled thereto, the strap configured to couple to the knee brace or a component coupled thereto and further configured to wrap around the user's shoulder so that the knee brace is maintained around at least part of the user's knee. In another embodiment, the knee brace comprises at least one brace connection portion adapted therein and/or coupled thereto, said connection portion configured to couple to the strap and/or the optional strap connection portion adapted in the strap and/or coupled to the strap. In yet another embodiment, the brace connection portion is selected from the group consisting of one or more loops, snaps, buttons, clips, hooks, clasps, and ties. In an additional embodiment, the brace connection portion defines one or more apertures therein.

In an exemplary embodiment of a knee brace system of the present disclosure, the strap further comprises the optional strap connection portion. In an additional embodiment, the optional strap connection portion is selected from the group consisting of one or more loops, snaps, buttons, clips, hooks, clasps, and ties. In yet an additional embodiment, the optional strap connection portion defines one or more apertures therein. In another embodiment, the knee brace comprises at least one brace connection portion adapted therein and/or coupled thereto, said connection portion configured to couple to the strap and/or the optional strap connection portion adapted in the strap and/or coupled to the strap.

In an exemplary embodiment of a knee brace system of the present disclosure, the system further comprises an interim connector configured to couple to the knee brace. In another embodiment, the system further comprises an interim connector configured to couple to the brace connection portion. In yet another embodiment, the system further comprises an interim connector configured to couple to the strap. In an additional embodiment, the system further comprises an interim connector configured to couple to the optional strap connection portion.

In an exemplary embodiment of a knee brace system of the present disclosure, the knee brace comprises at least one brace connection portion adapted therein and/or coupled thereto, wherein the strap further comprises the optional strap connection portion, and wherein the system further comprises an interim connector configured to couple to the brace connection portion and the optional strap connection portion. In an additional embodiment, the interim connector is selected from the group consisting of one or more loops, snaps, buttons, clips, hooks, clasps, and ties. In yet an additional embodiment, the interim connector defines one or more apertures therein. In another embodiment, the optional strap connection portion is positioned at a first end of the strap.

In an exemplary embodiment of a knee brace system of the present disclosure, a first end of the strap is configured to couple to the knee brace or to a brace connection portion coupled thereto. In another embodiment, the strap further comprises the optional strap connection portion positioned at a first end of the strap, and wherein the optional strap connection portion is configured to couple to the knee brace or to a brace connection portion coupled thereto. In yet another embodiment, a second end of the strap is also configured to couple to the knee brace or to the brace connection portion coupled thereto. In an additional embodiment, the strap further comprises a second strap connection portion positioned at a second end of the strap, and wherein the second strap connection portion is also configured to couple to the knee brace, the brace connection portion coupled thereto, or to a second brace connection portion coupled to the knee brace.

In an exemplary embodiment of a knee brace system of the present disclosure, the strap comprises a self-joining portion adapted therein and/or coupled thereto. In another embodiment, the strap self-joining portion is configured to couple to a first end of the strap, a second end of the strap, and/or the optional strap connection portion. In yet another embodiment, the strap self-joining portion is selected from the group consisting of one or more loops, snaps, buttons, clips, hooks, clasps, and ties. In an additional embodiment, the strap self-joining portion defines one or more apertures therein. In yet an additional embodiment, the first end of the strap or the optional strap connection portion is configured to couple to one or more of the knee brace, an optional brace connection portion adapted therein and/or coupled to the knee brace, and/or an interim connector coupled to one of the aforementioned components, and wherein a second end of the strap or an optional second strap connection portion is configured to couple to one or more of another portion of the strap at the strap self-joining portion.

In an exemplary embodiment of a knee brace system of the present disclosure, the system is configured so that when the user is wearing the system and the knee brace is positioned on the user's left knee and when the strap is coupled thereto, a portion of the strap is positioned over or around the user's opposing right shoulder. In an additional embodiment, in the system is configured so that when the user is wearing the system and the knee brace is positioned on the user's right knee and when the strap is coupled thereto, a portion of the strap is positioned over or around the user's opposing left shoulder. In yet an additional embodiment, the system is further configured so not to eliminate weightbearing of an afflicted leg wearing the knee brace. In another embodiment, the system is further configured so that the user does not require a crutch or a cane in order to walk while wearing the system.

In an exemplary embodiment of a knee brace system of the present disclosure, the system is further configured to maintain a vertical position of the knee brace, or to prevent downward slippage of the knee brace, when the user wears the system. In another embodiment, the vertical position is maintained or the downward slippage is prevented without the need for a second strap positioned around the user's torso. In yet another embodiment, the system is further configured to maintain a vertical position of the knee brace, or to prevent downward slippage of the knee brace, when the user wearing the system is obese or otherwise overweight.

In an exemplary embodiment of a method of using a system of the present disclosure, the method comprises the steps of (a) positioning a knee brace around at least part of a user's knee, (b) coupling a strap, having an optional strap connection portion coupled thereto, to the knee brace or a component coupled thereto, and (c) wrapping at least part of the strap around a shoulder of the user so that the knee brace is maintained around at least part of the user's knee, wherein steps (a), (b), and (c) are performed in any order.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 1A:
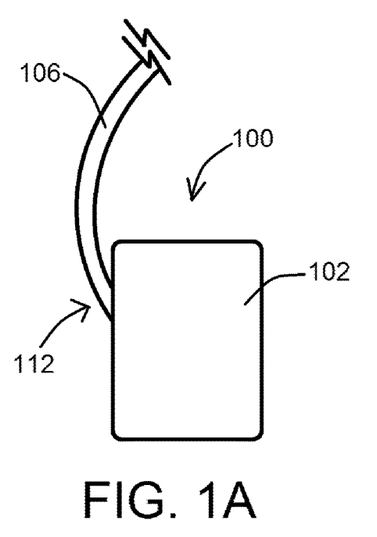
FIG. 1A shows a portion of a system having a knee brace and a strap coupled thereto, according to an exemplary embodiment of the present disclosure.
Figure 1B:
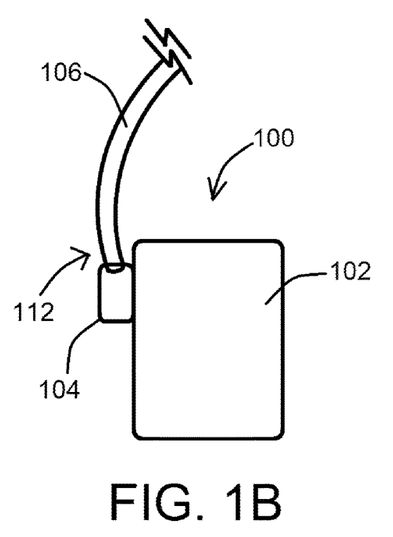
FIG. 1B shows a portion of a system having a knee brace and a strap coupled to a brace connection portion, according to an exemplary embodiment of the present disclosure.
Figure 1C:
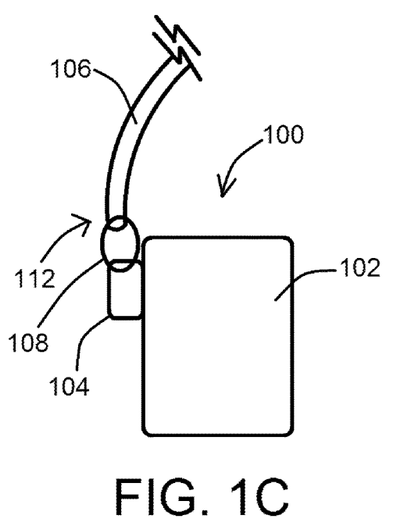
FIG. 1C shows a portion of a system having a knee brace and a strap coupled to a strap connection portion, according to an exemplary embodiment of the present disclosure.

Exemplary knee brace systems of the present disclosure are shown in FIGS. 1A-1D. As shown in FIG. 1A, system 100 comprises a knee brace 102 configured to fit around at least part of a user's knee and/or an area of the user's leg above and/or below the knee. As referenced herein, a user 200 may wear some or all of an exemplary system 100 of the present disclosure, such as knee brace 102, around the user's leg 202 at or near the knee 204. Knee braces 102 of the present disclosure may have at least one brace connection portion 104 adapted therein and/or coupled thereto, as shown in FIG. 1B, said brace connection portion 104 configured to couple to a strap 106 and/or a strap connection portion 108 adapted in strap 106 and/or coupled to strap 106. Brace connection portion 104 and/or strap connection portion 108, as shown in FIG. 1C, of the present disclosure can include/comprise/form one or more loops, snaps, buttons, clips, hooks, clasps, ties, and or other connector(s) known in the art, and/or define/include one or more apertures therein. For example, an exemplary brace connection portion 104 may comprise a clasp, and an exemplary strap connection portion 108 may comprise a loop, whereby the clasp can engage the loop. Exemplary knee braces 102 of the present disclosure may also be adjustable so to allow the user 200 to comfortably place knee brace 102 around the user's 200 knee 204.

Figure 1D:
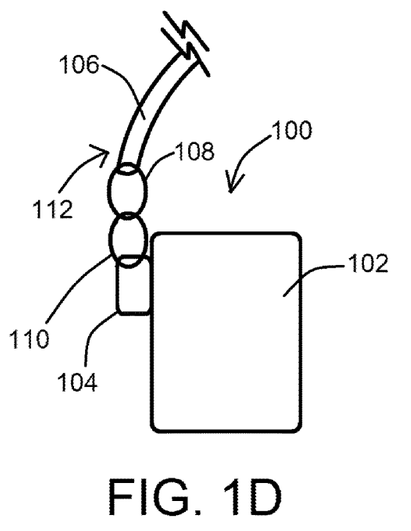
FIG. 1D shows a portion of a system having a knee brace and a strap indirectly coupled thereto using a strap connection portion, an interim connector, and a brace connection portion, according to an exemplary embodiment of the present disclosure.

Exemplary knee braces 102 and/or straps 106 may not each comprise a brace connection portion 104 and/or a strap connection portion 108. For example, and as shown in FIGS. 1A and 1B, a strap 106 may not have a separate strap connection portion 108 adapted therein and/or coupled thereto, and in such an embodiment, a portion of said strap 106 would be configured to couple to an exemplary brace connection portion 104, such as an aperture defined therein. Exemplary systems 100 of the present disclosure are intended to include a knee brace 102 and a strap 106, whereby knee brace 102 either directly or indirectly couples to strap 106, and in at least some embodiments, said components are configured to reversibly couple to one another, either directly as referenced above, using a brace connection portion 104 and/or a strap connection portion 108 also as referenced above, and/or using one or more interim connectors 110 therebetween as shown in FIG. 1D. In view of the same, one or more interim connectors 110 would be configured to couple to one or more of a knee brace 102, a brace connection portion 104, a strap 106, and/or a strap connection portion 108. Interim connectors 110, similar to brace connection portions 104 and strap connection portions 108 referenced above, may comprise one or more loops, snaps, buttons, clips, hooks, clasps, ties, and or other connector(s) known in the art, and optionally defining one or more apertures therethrough.

Figure 2A:
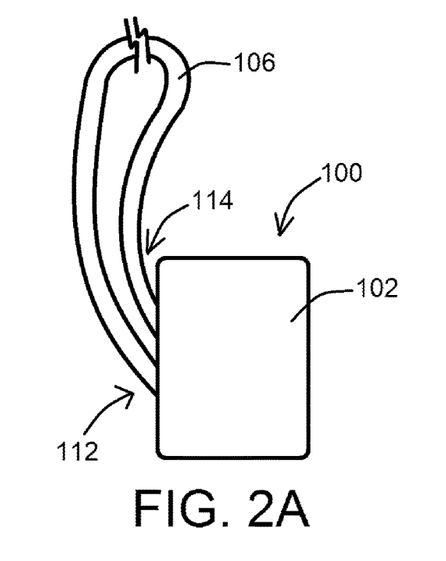
FIG. 2A shows a portion of a system having a knee brace and two ends of a strap coupled thereto, according to an exemplary embodiment of the present disclosure.
Figure 2B:
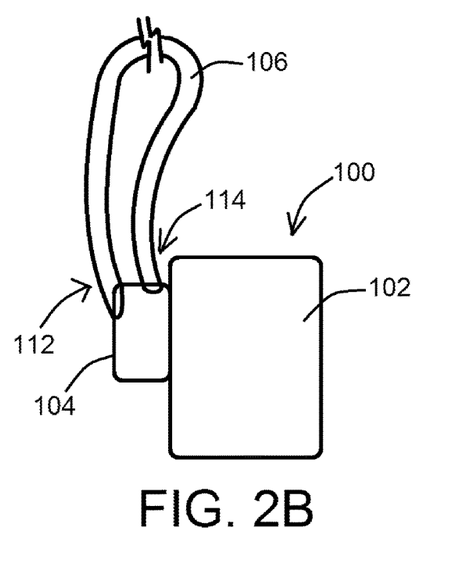
FIG. 2B shows a portion of a system having a knee brace and two ends of a strap coupled to a brace connection portion, according to an exemplary embodiment of the present disclosure.
Figure 2C:
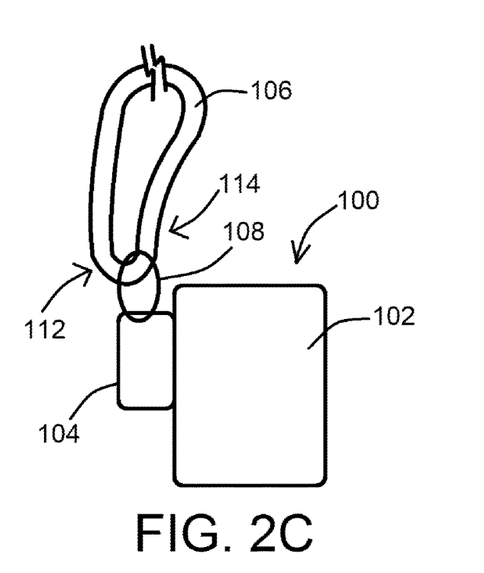
FIG. 2C shows a portion of a system having a knee brace and two ends of a strap coupled to a strap connection portion, according to an exemplary embodiment of the present disclosure.

In various embodiments of systems 100 of the present disclosure and as shown in FIG. 2C, a first end 112 of strap 106 and/or a second end 114 of strap 106 is/are configured to engage knee brace 102 and/or a brace connection portion 104 of knee brace 102 and/or one or more interim connectors 110 coupled thereto. The terms "first end" and second end" are not limited to the very end of a strap 106, but is/are intended to relate to relative end portions/sections of strap 106. For example, if a strap 106 was visually divided into thirds, the first third could be considered as being first end 112 of strap 106, the second third could be considered as a relative middle of strap 106, and the third could be considered as being second end 114 of strap 106.

In at least one embodiment, first end 112 of strap 106 is configured to couple to brace connection portion 104 of knee brace 102, such as shown in FIGS. 1B and 2B. In another embodiment, and as shown in FIG. 2B, first end 112 of strap 106 is configured to couple to a first brace connection portion 104 of knee brace 104, and second end 114 of strap 106 is configured to couple to the same first brace connection portion 104 and/or to a second brace connection portion 104. In other embodiments, one or both of first end 112 and second end 114 of strap are configured to couple directly to knee brace 102 or to an interim connector 110, as shown in FIG. 2C.

Figure 2D:
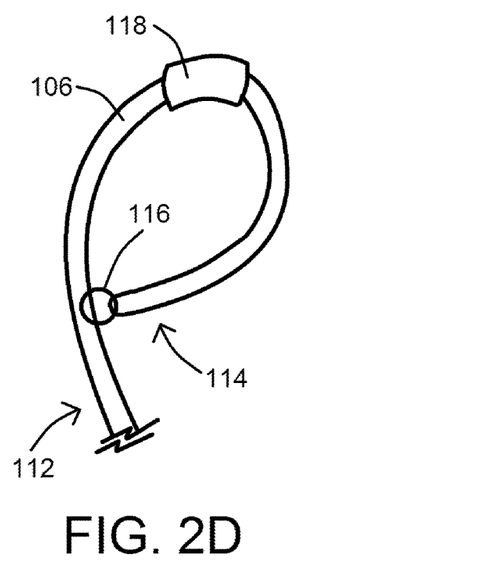
FIG. 2D shows a portion of a system having a strap coupled to itself using a strap self-joining portion, according to an exemplary embodiment of the present disclosure.

In at least one embodiment, one end of strap 106 (such as first end 112 or second end 114) is configured to couple to knee brace 102, brace connection portion 104, or interim connector 110, and the other end of strap 106 is configured to couple to a portion of strap 106 or to a component coupled to strap 106. For example, and as shown in FIG. 2D, strap 106 may have a strap self-joining portion 116 adapted therein and/or coupled thereto, said strap self-joining portion 116 configured to couple to a first end 112 of strap 106, a second end 114 of strap 106, and/or a strap connection portion 108. Strap self-joining portions 116 of the present disclosure can include/comprise/form one or more loops, snaps, buttons, clips, hooks, clasps, ties, and or other connector(s) known in the art, and/or define/include one or more apertures therein. For example, and in an exemplary embodiment, first end 112 (or a first strap connection portion 108) of strap 106 is configured to couple to knee brace 102, brace connection portion 104, and/or interim connector 110, and a second end 114 (or a first or another strap connection portion 108) of strap 106 may be configured to couple to another portion of strap 106 (such as by the user's 200 armpit, side of chest, side of abdomen, hip, or side of thigh) at strap self-joining portion 116.

In such embodiments, and when a user 200 is wearing system 100 and knee brace 102 is positioned on the user's 200 left knee 204 and when strap 106 is coupled thereto, a portion of strap 106 is positioned over or around the user's 200 opposing right shoulder 206. Similarly, and when a user 200 is wearing system 100 and knee brace 102 is positioned on the user's 200 right knee 204 and when strap 106 is coupled thereto, a portion of strap 106 is positioned over or around the user's 200 opposing left shoulder 206. Should a user 200 wear two knee braces 102, a first strap 106 would extend from the left knee brace 102 to/over/around the right shoulder 206, and a second strap 106 would extend from the right knee brace 102 to/over/around the left shoulder 206.

Various systems 100 of the present disclosure are configured to provide a user 200 with various advantages. For example, an exemplary system 100 of the present disclosure is configured so not to eliminate weightbearing of the afflicted leg 202 wearing knee brace 102. Such an embodiment would allow a user 200 to bear body weight on the afflicted leg 202/knee 204 while wearing system 100, so to, for example, allow the user's 200 body to again get used to body weightbearing during rehabilitation. Various systems 100 of the present disclosure, when worn by a user 200, are configured so to permit user 200 mobility without requiring a crutch or a cane. For example, with systems that do not allow a user's 200 foot to either engage the ground while walking, or that are configured to allow a user's 200 foot to engage the ground while walking but not to allow for most or full weight bearing, the user 200 would also need to use a crutch or a cane for mobility. As such, various systems 100 of the present disclosure, when worn by a user 200, do not negatively impact user 200 mobility.

Furthermore, various systems 100 of the present disclosure are configured to maintain a vertical position of knee brace 102, or to prevent downward slippage of knee brace 102, without the need for a second strap positioned around a user's 200 torso 208. For example, if a knee brace 102 has a relative middle portion wrapping around a user's 200 knee 204, and upper and lower portions above and below the relative middle portion, use of said knee brace 102 within system 100, would maintain the positioning of knee brace 102 around the user's 200 knee and/or prevent knee brace 102 from slipping downward. In view of the same, various systems 100 of the present disclosure are configured to assist an obese or otherwise overweight person maintain a vertical position of knee brace 102 around the knee 204, as an obese or otherwise overweight person may have a relatively large thigh having a width tapering outward moving up the thigh, and with such a bodily shape, a knee brace 102 would be prone to slippage or otherwise generally difficult, if not impossible, to keep in place. Systems 100 of the present disclosure can be used for such users 200, so that when strap 106 is properly secured to knee brace 102 and worn over the user's 200 opposite shoulder 206, knee brace 102 maintains its position around the user's 200 knee 204.

In various other embodiments of the present disclosure, strap 106 may be worn around the shoulder 206 on the same side of the user's 200 body where knee brace 102 is secured.

Figure 3:
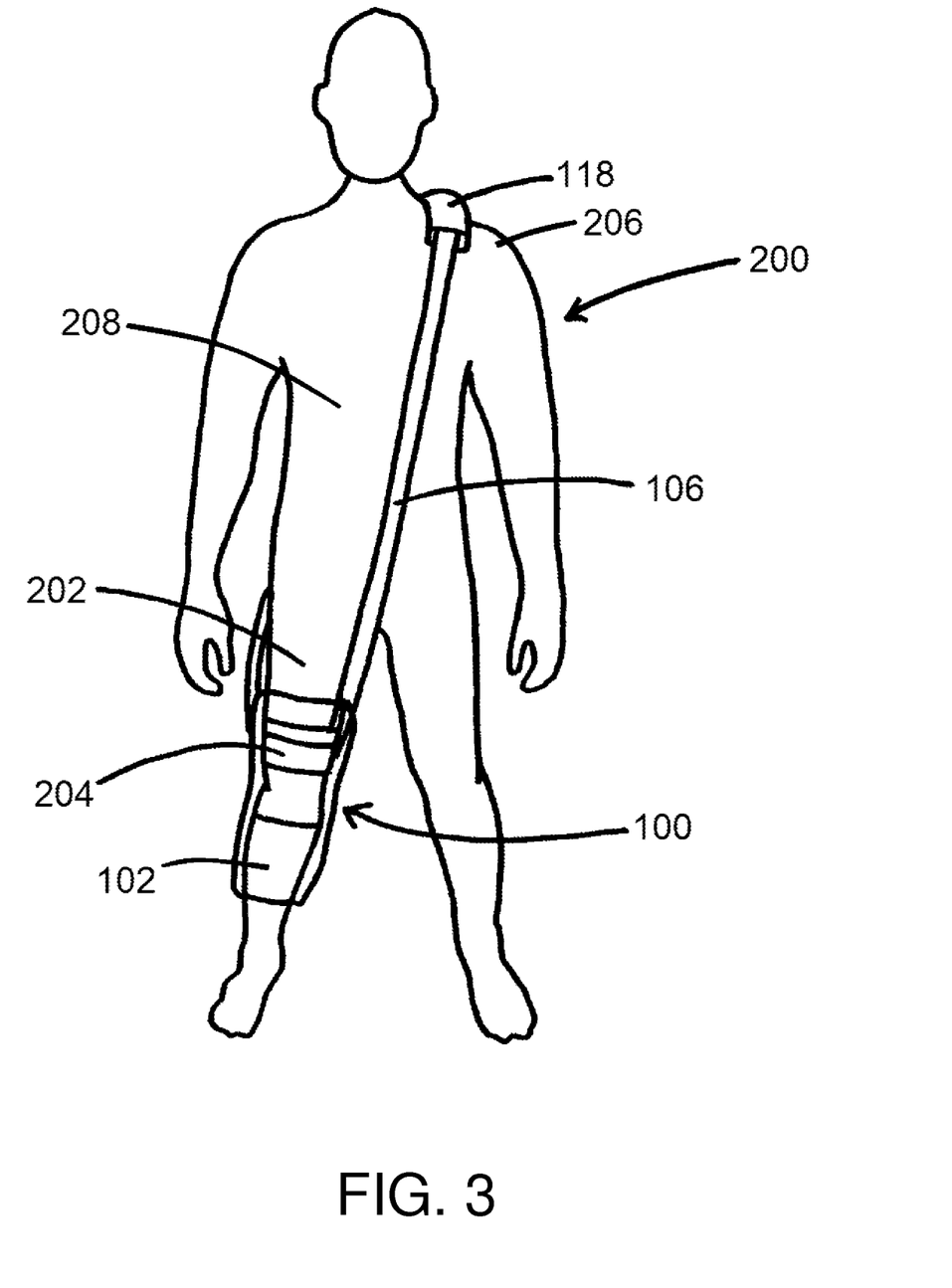
FIGS. 3 and 4 show a user wearing a system, according to an exemplary embodiment of the present disclosure.
Figure 4:
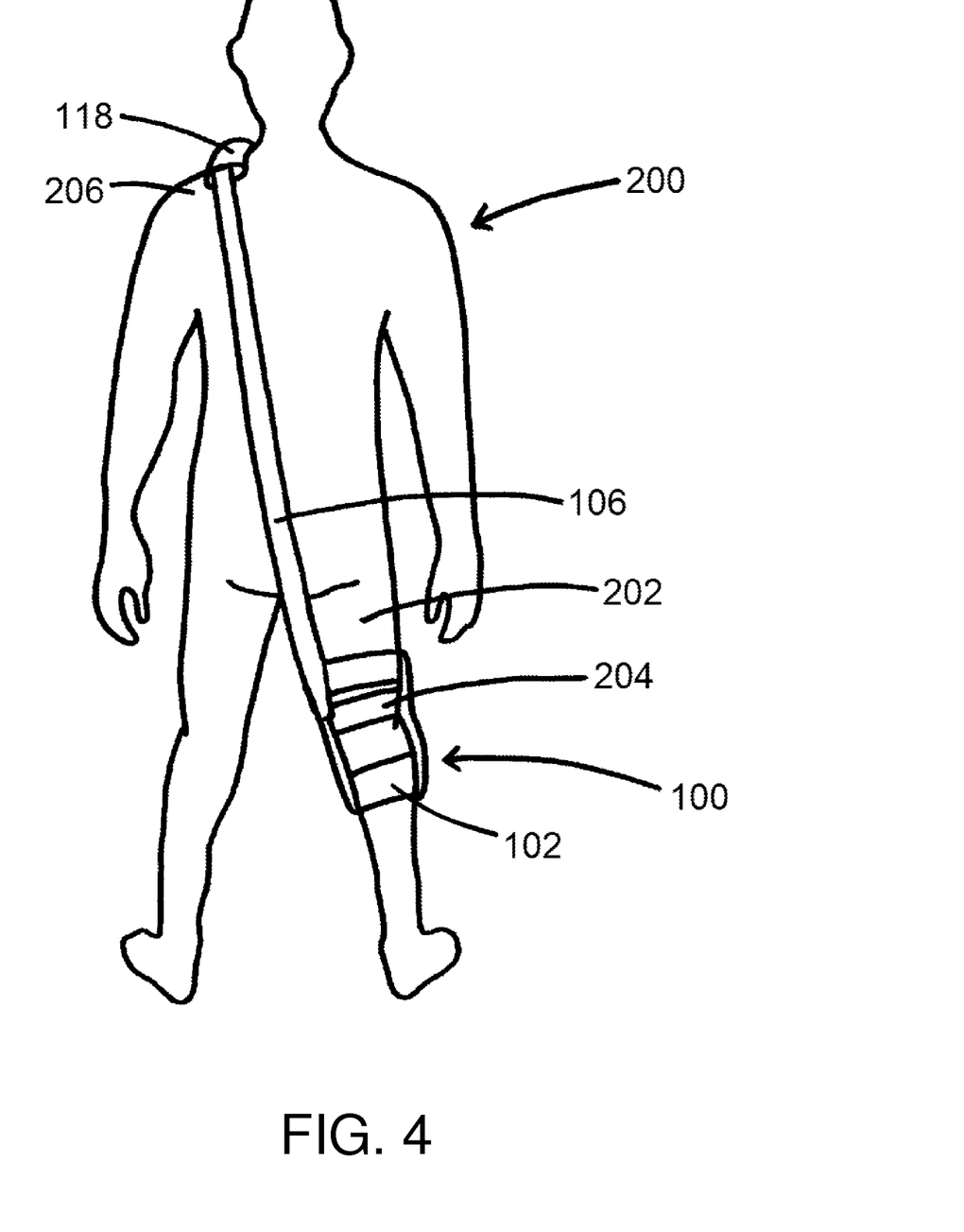

FIGS. 3 and 4 show a user 200 wearing system 100, with knee brace 102 and strap 106 shown in each figure. FIG. 3 also shows an optional cushion 118, coupled to or positioned adjacent to a portion of strap 106, whereby cushion 118 provides some cushioning effect at or near the user's 200 shoulder 206, for example, to improve system wearability.

Figure 5:
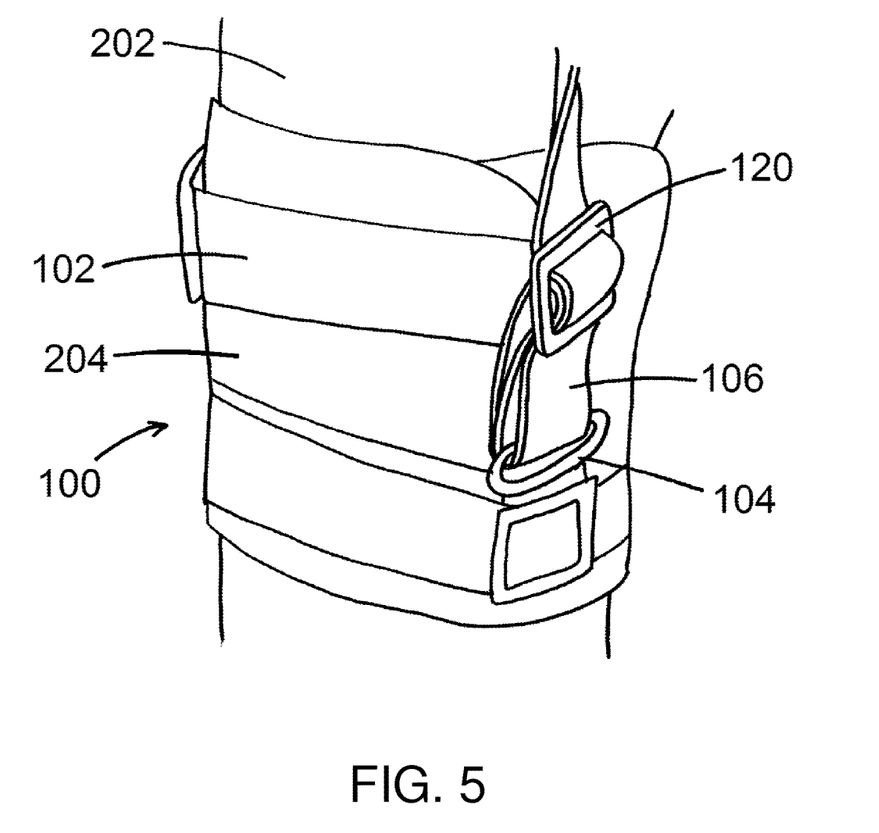
FIGS. 5 and 6 show close-up views of a user wearing a system, according to an exemplary embodiment of the present disclosure.
Figure 6:
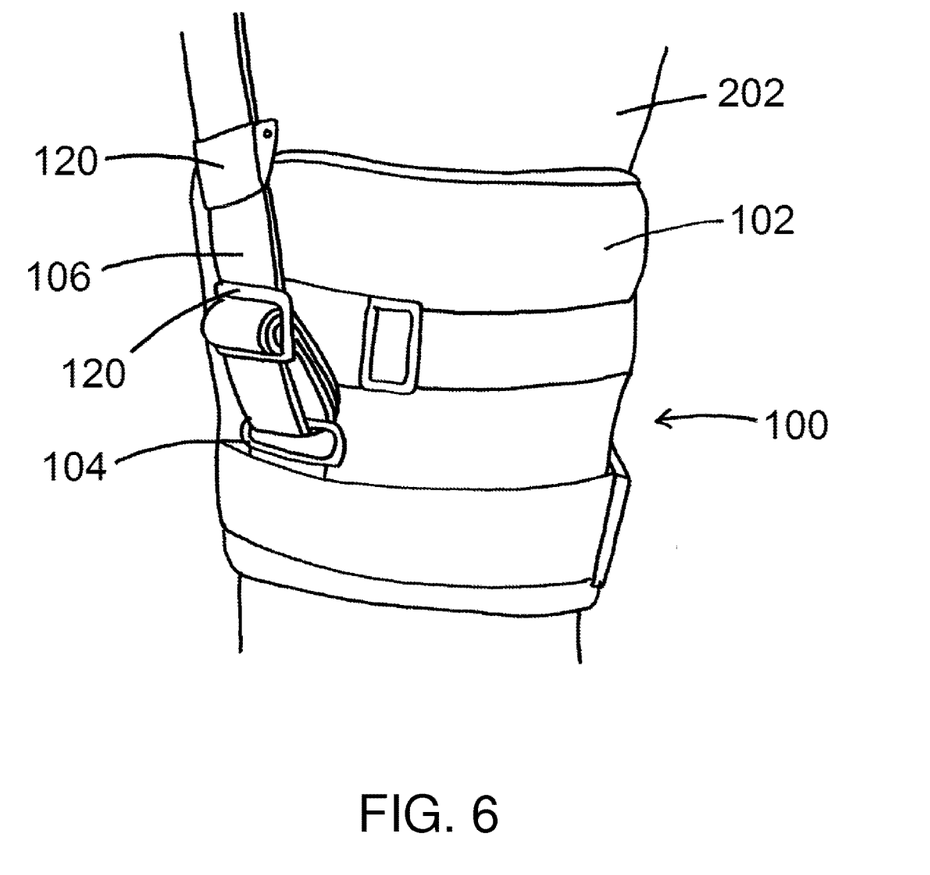

FIGS. 5 and 6 show close-up views of a user 200 wearing a knee brace 102 and strap 106. As shown therein, strap 106 may have one or more adjusters 120 coupled thereto, so that an effective length of strap 106 may be adjusted.

While various embodiments of knee brace systems and methods of using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A knee brace system, consisting of:
   a knee brace configured to fit around at least part of a user's knee;
   a strap coupled thereto, the strap configured to couple to the knee brace and further configured to wrap around a user's shoulder so that the knee brace is maintained around at least part of the user's knee; and
   a self-joining portion connected to the strap, the self-joining portion comprising a connector configured as a loop and defining an aperture therethrough;
   wherein a first end of the strap is coupled to the knee brace and wherein a second end of the strap is coupled to the loop of the self-joining portion wherein the self-joining portion is configured to couple to at least one of the first end of the strap, the second end of the strap or a strap connection portion configured to couple to the knee brace.

2. The system of claim 1, wherein the knee brace comprises at least one brace connection portion coupled thereto, said brace connection portion configured to couple to the strap.

3. The system of claim 2, wherein the brace connection portion is selected from the group consisting of one or more loops, one or more snaps, one or more buttons, one or more clips, one or more hooks, one or more clasps, and one or more ties.

4. The system of claim 2, wherein the brace connection portion defines one or more apertures therein.

5. The system of claim 1, further comprising:
   an interim connector configured to couple to the knee brace.

6. The system of claim 1, wherein the knee brace comprises at least one brace connection portion adapted therein, wherein the strap further comprises a strap connection portion coupled thereto, and wherein the system further comprises:
   an interim connector configured to couple to the brace connection portion and the strap connection portion.

7. The system of claim 6, wherein the strap connection portion is positioned at a first end of the strap.

8. The system of claim 1, wherein the strap further comprises a strap connection portion positioned at a first end of the strap, and wherein the strap connection portion is configured to couple to the knee brace or to a brace connection portion coupled thereto.

9. The system of claim 8, wherein the strap further comprises a second strap connection portion positioned at a second end of the strap, and wherein the second strap connection portion is also configured to couple to the knee brace, the brace connection portion coupled thereto, or to a second brace connection portion coupled to the knee brace.

10. The system of claim 1, wherein the system is further configured so not to eliminate weightbearing of an afflicted leg wearing the knee brace.

11. The system of claim 1, wherein the system is further configured so that the user does not require a crutch or a cane in order to walk while wearing the system.

12. The system of claim 1, wherein the system is further configured to maintain a vertical position of the knee brace, or to prevent downward slippage of the knee brace, when the user wears the system.

13. The system of claim 12, wherein the vertical position is maintained or the downward slippage is prevented without the need for a second strap positioned around the user's torso.

14. The system of claim 1, wherein the system is further configured to maintain a vertical position of the knee brace, or to prevent downward slippage of the knee brace, when the user wearing the system is obese or otherwise overweight.

15. A knee brace system, consisting of:
   a knee brace configured to fit around at least part of a user's knee, the knee brace comprising at least one brace connection portion coupled thereto and defining one or more apertures therein; and
   a strap having a strap connection portion coupled thereto, the strap configured to couple to the brace connection portion of the knee brace and further configured to wrap around a user's shoulder so that the knee brace is maintained around at least part of the user's knee; and
   a self-joining portion connected to the strap, the self-joining portion comprising a connector configured as a loop and defining an aperture therethrough;
   wherein a first end of the strap is coupled to the brace connection portion and wherein a second end of the strap is coupled to the self-joining portion wherein the self-joining portion is configured to couple to at least one of the first end of the strap, the second end of the strap or a strap connection portion configured to couple to the knee brace; and
   wherein the system is configured to prevent downward slippage of the knee brace when the user wears the system.

16. A method of using a knee brace system, the knee brace system consisting of:
   a knee brace configured to fit around at least part of a user's knee,
   a strap coupled thereto, the strap configured to couple to the knee brace and further configured to wrap around a user's shoulder so that the knee brace is maintained around at least part of the user's knee, and
   a self-joining portion connected to the strap, the self-joining portion comprising a connector configured as a loop and defining an aperture therethrough,
   wherein a first end of the strap is configured to be coupled to the knee brace and wherein a second end of the strap is configured to be coupled to the loop of the self-joining portion;
   the method comprising the steps of:
   (a) positioning the knee brace around at least part of the user's knee;
   (b) coupling the first end of a strap to the knee brace;
   (c) wrapping at least part of the strap around the user's shoulder so that the knee brace is maintained around at least part of the user's knee;
   (d) connecting a second end of the strap to the self-joining portion wherein the self-joining portion is configured to couple to at least one of the first end of the strap, the second end of the strap or a strap connection portion configured to couple to the knee brace; and
   (e) adjusting a length of the strap after the strap is coupled to the knee brace;
   wherein steps (a), (b), and (c) are performed in any order.

17. The method of claim 16, wherein the system is configured so that when the user is wearing the system and the knee brace is positioned on the user's left knee and when the strap is coupled thereto, a portion of the strap is positioned over or around the user's opposing right shoulder.

18. The method of claim 16, wherein the system is configured so that when the user is wearing the system and the knee brace is positioned on the user's right knee and when the strap is coupled thereto, a portion of the strap is positioned over or around the user's opposing left shoulder.

19. The system of claim 1, further comprising:
a cushion coupled to or positioned adjacent to a portion of the strap, the cushion providing a cushioning effect at or near a shoulder of a user wearing the system; and
an adjuster coupled to the strap and configured to allow an effective length of the strap to be adjusted.

* * * * *